United States Patent [19]

Jonsson et al.

[11] Patent Number: 4,919,119
[45] Date of Patent: Apr. 24, 1990

[54] EXTERNAL DYNAMIC BONE FIXATION DEVICE

[75] Inventors: Ulf Jonsson, Lidingo, Sweden; Marcel Wagenknecht, Le Lignon, Switzerland

[73] Assignee: Jaquet Orthopedie, S.A., Geneva, Switzerland

[21] Appl. No.: 863,756

[22] Filed: May 16, 1986

[51] Int. Cl.⁵ .................................................. A61F 5/04
[52] U.S. Cl. ................................................................ 606/54
[58] Field of Search ........ 128/92 ZZ, 92 ZY, 92 ZK, 128/92 ZW, 92 Z, 80 C, 80 F, 88

[56] References Cited

U.S. PATENT DOCUMENTS

| Re. 31,809 | 1/1985 | Danielletto et al. | 128/92 ZZ |
|---|---|---|---|
| 1,997,466 | 4/1935 | Longfellow | 128/92 ZZ |
| 3,779,654 | 12/1973 | Horne | 128/80 C |
| 3,941,123 | 3/1976 | Volkov et al. | 128/84 B |
| 4,185,623 | 1/1980 | Volkov et al. | 128/92 Z |
| 4,337,764 | 7/1982 | Lerman | 128/80 F |
| 4,393,868 | 7/1983 | Teague | 128/92 A |
| 4,397,308 | 8/1983 | Hepburn | 128/80 F |
| 4,440,159 | 4/1984 | Cochran | 128/84 R |
| 4,488,542 | 12/1984 | Helland | 128/92 ZK |
| 4,523,585 | 6/1985 | Lamb et al. | 128/80 C |
| 4,541,422 | 9/1985 | de Zbikowski | 128/92 ZW |
| 4,548,199 | 10/1985 | Agie | 128/92 ZK |
| 4,554,915 | 11/1985 | Brumfield | 128/92 A |
| 4,611,586 | 9/1986 | Agee et al. | 128/92 A |
| 4,612,919 | 9/1986 | Best | 128/77 |
| 4,618,147 | 10/1986 | Hurd et al. | 273/54 B |
| 4,620,532 | 11/1986 | Housworth | 128/80 C |
| 4,628,919 | 12/1986 | Clyburn | 128/92 ZZ |
| 4,637,382 | 1/1987 | Walker | 128/80 F |
| 4,643,177 | 2/1987 | Sheppard et al. | 128/84 C |
| 4,696,293 | 9/1987 | Ciullo | 128/92 Z |
| 4,699,129 | 10/1987 | Aaserude et al. | 128/80 C |
| 4,730,608 | 3/1988 | Schlein | 128/92 ZK |
| 4,782,842 | 11/1988 | Fietti | 128/92 Z |

FOREIGN PATENT DOCUMENTS

| 0177270 | 4/1986 | European Pat. Off. | |
|---|---|---|---|
| 2745504 | 4/1979 | Fed. Rep. of Germany | 128/92 ZW |
| 0888978 | 12/1981 | U.S.S.R. | 128/92 ZY |

Primary Examiner—Stephen C. Pellegrino
Assistant Examiner—Ralph Lewis
Attorney, Agent, or Firm—Peter C. Richardson; Lawrence C. Akers; Elizabeth O. Slade

[57] ABSTRACT

An external fixation device for the fixation of a broken joint includes first and second fixation rods connected to bone pins intended to be introduced into the bone, and an articulating portion joining the two rods. One of the two fixation rods is connected to a sliding block that slides within the housing of the articulating portion upon a sliding surface having a virtual axis. The articulating portion housing is provided with viewing lines on its cover for accurately sighting the location of the articulation axis of the prosthetic joint.

16 Claims, 2 Drawing Sheets

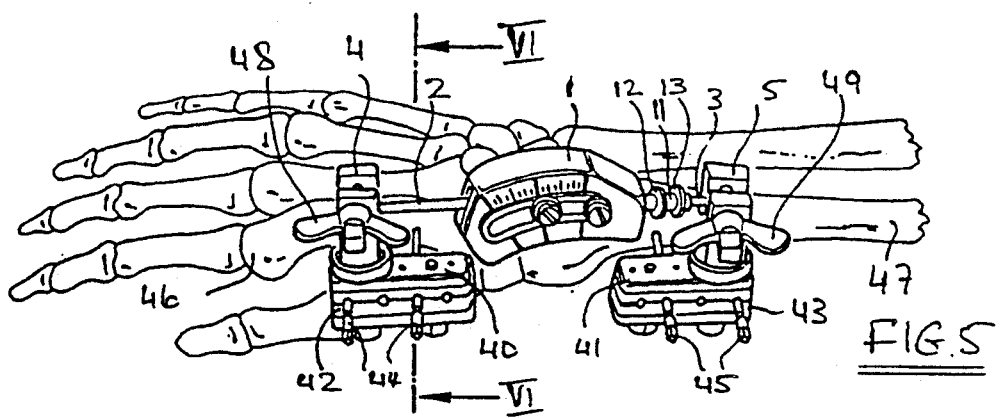
FIG.5
FIG.6
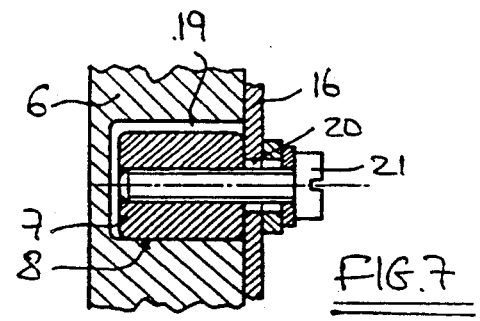
FIG.7
FIG.8

EXTERNAL DYNAMIC BONE FIXATION DEVICE

BACKGROUND OF THE INVENTION

The present invention relates to medical equipment and more particularly to an apparatus for bone fixation allowing the movement of bones at a broken joint.

For the purposes of this invention, such a fixation is termed a "dynamic fixation". This designates a bone fixation, by means of pins, bars and external supports, which has an articulation in geometrical relationship with an articulation of the human or animal body, allowing the fixation of bone fragments of each one of the bones which are articulated, but allowing also a pivoting movement of the parts of the fixation device about their axis of articulation.

External anchoring or fixing of bones is an old surgical technique which was first used a century ago. Its application has for a long time been limited to complicated fractures in traumatology and consequently in orthopedics, i.e. the secondary treatment of fractures, infections, slow knitting of the bones, pseudarthroses, difficult bone-settings, etc. External anchoring is used particularly for long bones such as the femur, the tibia, the humerus, the radius and the cubitus. However, it is also desirable to manufacture small anchoring means which can be used on small bones, such as the metatarsals and the metacarpals, and in maxillofacial surgery as well as in experimental surgery on small animals.

External bone-anchoring elements enable two kinds of bone-anchoring to be carried out:

transfixing anchoring, wherein the pins extend from one side of the limb to the other, and non-transfixing anchoring, wherein the pins are introduced into the bone without completely transversing it.

Transfixing anchorage, which is mostly used on the leg, is more rigid than non-transfixing anchorage. At both sides of the bone are fitted two rods or frames, upon which are anchored two groups of pins disposed on either side of the fracture. The two frames or the two rods are interconnected by a brace which is as stable as possible and which may comprise sliding rods or bars, the length of which can be increased or reduced.

Thus the basic techniques of external bone fixation are already known. Consideration has already been given to extending external bone fixation to the osteosynthesis of broken joints. This idea was to fix the bone fragments of the broken joint parts to the adjacent bones by means of thin pins, to introduce fixation pins into the other member of the joint (which may also be broken or not) also, and to join these two parts of the external fixation device by an articulation coupling. The purpose of this articulated fixation is the following. Normally, a rigid bone fixation would be a sufficient means for curing the broken bone. However, when this broken bone is part of a joint, there is a great risk that the joint will remain stiff after healing, and it is considered as absolutely necessary that the patient make movement exercises with his broken joint as soon as possible. Such movements should begin with a small angle of flexion which will gradually be increased. All these movements must of course be permitted by the mounted external fixation device, and that is not the case with the rigid fixation device described, for example, in U.S. Pat. No. 4,365,624.

A dynamic external fixation device has been described in the French Patent Application No. 2,551,650 published March 15, 1985, of Terry A. Clyburn. This fixation device comprises, following the general idea mentioned above, a first proximal branch and a second distal branch, these branches being adapted for fixably receiving fixation pins, and a universal joint, typically a ball joint, linking said two branches.

In order to function correctly, the fixation device must of course be applied strictly in such a manner that the point of articulation between said branches of the device will lie exactly on the pivot axis of the wrist joint; otherwise, undue and painful tensions or compressions occur when the hand is to be moved with respect to the arm. However, this axis of articulation in the joints is in most cases not detectable with sufficient precision when there is a fresh fracture, all of the area being swollen and the joint not being pivotable. Furthermore, the location of the articulation point of this known device cannot be adjusted.

SUMMARY OF THE INVENTION

It is a first and primary object of this invention to provide a new and useful dynamic external bone fixation device for the healing of bone fractures in the joint area which does not suffer from the disadvantages listed above.

Another object of this invention is to provide a fixation device of the kind mentioned above which allows exercise of the injured joint, under gradually increasing angles and with controllable moving resistance.

Still another object of the invention is to provide a fixation device which can be positioned by the surgeon in a very exact manner with respect to the pivot axis of the injured joint, and which can be adjusted, as to the extent of articulation, even after the setting of the fixation pins.

A further object of this invention is to provide a dynamic external bone fixation device for application to broken joints which further permits a compression or extension treatment in the course of the healing period of the bones so that there is a perfect reconstitution of the joint and of its mobility.

These and still other objects are met by the dynamic external bone fixation device of this invention which comprises: (1) a first part having a fixation rod adapted to be connected to bone pins introduced into the bone on one side of a broken joint, (2) a second part having a fixation rod adapted to be connected to bone pins introduced into the bone on the other side of said joint, and (3) an articulating portion joining said two parts, said articulating portion having a curved sliding surface, said sliding surface having a virtual axis, and said articulating portion including means for aiming at the axis of said curved sliding surface.

In order to make the terms and notions of the art more easily understood, reference is made to U.S. Pat. No. 4,365,624, which is incorporated herein by reference in its entirety.

It has surprisingly been found that the device of the invention can not only be used with wrist fractures but also with fractures of other joints such as the knee, ankle, finger, elbow, shoulder and even the pelvis and collarbone.

The dynamic external bone fixation device of this invention has been developed from the basic idea than the device should not be placed laterally to the fractured joint of the body, in such a way that the center of articulation of the two fixation parts lies also in the pivot axis of said joint, but generally vertically to the joint, namely in a plane higher than the plane of the body. This will be explained below and illustrated in the figures.

This displacement of the point of articulation of the instant fixation device results in another geometrical implementation; the simple pivoting movement of a universal or ball joint, as known before, is to be replaced by a simultaneous pivoting and extension (or contraction) movement. Thus, the invention provides, besides two fixation parts to be fixed in the bones on both sides of the fractured joint, an articulating portion comprising curved, preferably cylindrically curved, sliding surfaces; one of these surfaces is convex and is a part of a "positive" element connected to one of said fixation parts, and the other one is concave and is a part of a "negative" element connected to the other fixation part. When these surfaces slide one over the other, one skilled in the art easily understands that the elements fixed to either surface will make a combined angular and longitudinal movement.

The concave surface is a part of a sliding block which is able to slide on a corresponding convex surface in the interior of a housing. This housing has a lateral closure, being at a right angle to the axis of said curved surfaces. The closure and, preferably, the other lateral surface of the housing are provided with a plurality of straight lines having one point of intersection outside of the housing. This point of intersection (and therefore the direction of said lines) is selected so as to define the axis of the curvature of said sliding surfaces. This axis is also the pivoting axis of the bone joint. When the surgeon applies the fixation device of the invention to the body, he will be able to aim at the joint axis in looking along said lines. He will very easily find said axis, even if the joint region is swollen, and he has the possibility of readjusting, if possible, the fixation device of this invention, as will be explained later.

The sliding block may be fixed by a screw which traverses a slot in the housing. This slot is curved and follows the curvature of the sliding surfaces. Another screw, to be locked in said slot only, serves as a stop for limiting the movement of the sliding block in the housing. In the neighborhood of the slot, angle indications may be provided. The sliding surfaces may be covered by an antifrictional layer, for example of teflon (PTFE) or nylon.

The materials of the instant fixation device will be selected to withstand repeated sterilization. This selection of materials is conventional for the man skilled in the art.

Furthermore, it is preferred to control the movement of the sliding block in the housing with regard to the force necessary for displacing the sliding block, in order to be able to establish a suitable training or recovery program for the patient. In one group of embodiments, the sliding block movement is impeded by spring forces, be it a torsion spring or the elastic force of a rubber strip; in another embodiment, a frictional force is applied to said movement. The amount of said frictional force may preferably be controlled between nearly zero to complete blocking.

DETAILED DESCRIPTION OF THE INVENTION

In order to explain the dynamic external bone fixation device of this invention in more detail, several preferred embodiments thereof will be described with reference to the attached drawings wherein:

FIG. 5 is a perspective view of a dynamic external wrist fixation device comprising two groups of two pins each, these groups being connected to two corresponding bars, these bars being linked to the dynamic connection member.

FIG. 6 is a section view taken along line VI—VI in FIG. 5, in an embodiment in which the pins are angulated at 40°.

FIG. 7 is an partial view, taken in section along line VII—VII in FIG. 1, showing the connection member in a locked position.

FIG. 8 is an enlarged detail of FIG. 4 which illustrates an embodiment using a frictional brake to resist the patient's movement.

Figures 1, 2, 3, 4:
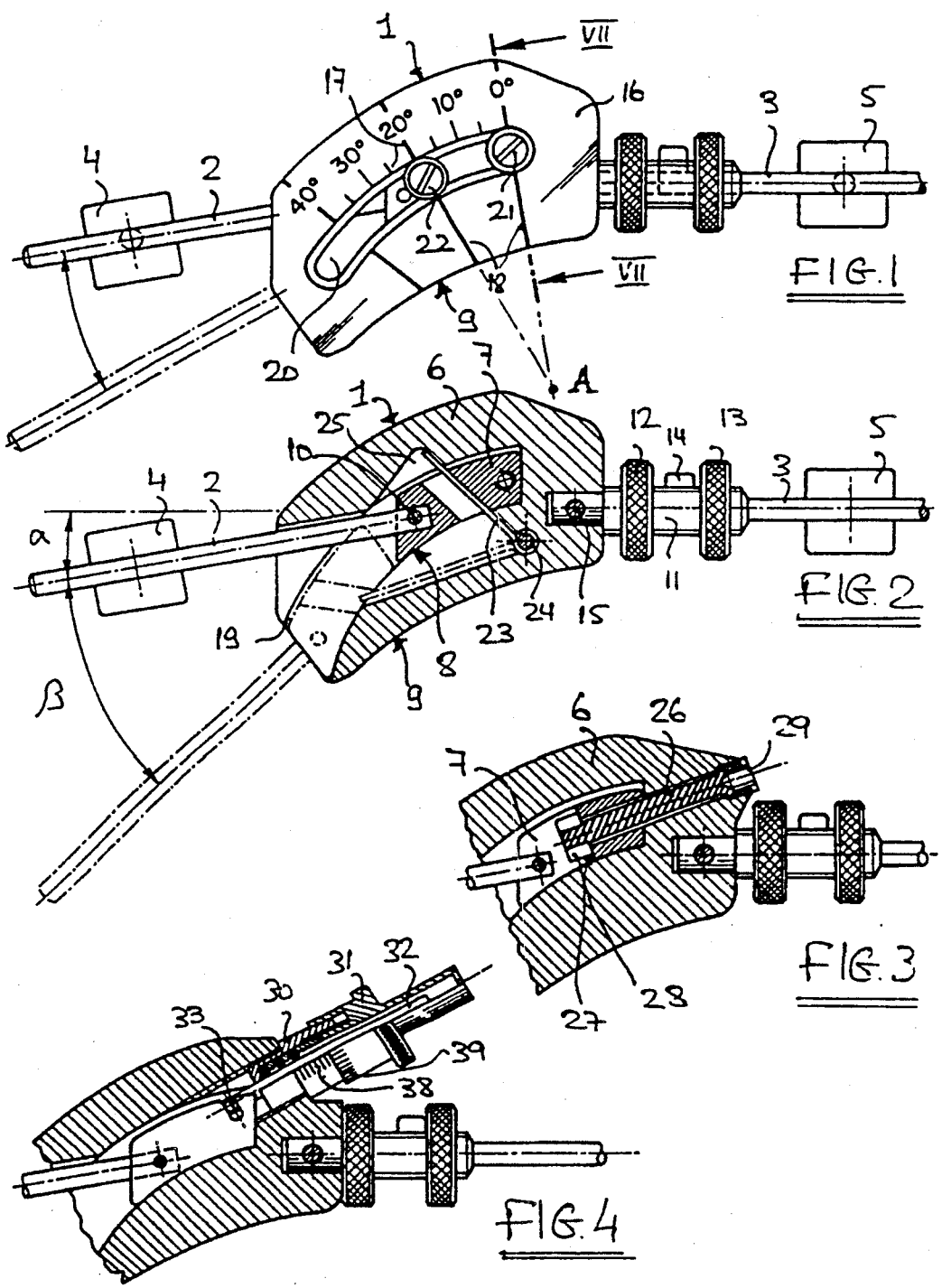
FIG. 1 is a lateral elevational view of a dynamic connection member showing the neutral position of the connection bars in full lines and their maximally permitted position in dotted lines.
FIG. 2 is a longitudinal sectional view of the connection member of FIG. 1, in a first embodiment including a spring to resist the patient's movement.
FIGS. 3 and 4 are partial views similar to FIG. 2, showing embodiments where biasing means are respectively an elastic member and a frictional brake.

The dynamic external bone fixation device represented in FIGS. 1 and 2 comprises an articulating portion 1 joining the rods 2 and 3.

As explained below, the rod 2 is to be connected to the pins fixed in the patient's metacarpus by means of a coupling schematized in 4. Similarly, the rod 3 is to be linked to the patient's radius by means of the coupling schematized in 5.

The articulating portion 1 is principally constituted of a housing 6 and of a sliding block 7 which are both capable of sliding with respect to a sliding surface 8.

In other terms, the housing 6 presents a convex sliding surface 8 whereas the sliding block 7 presents a corresponding concave sliding surface. These sliding surfaces are for example cylindrical surfaces, the axes of the corresponding cylinders being normal to the sliding plane of the articulating portion 1. In the drawings, this virtual axis is represented by A and corresponds to the axes of movement of the fractured wrist.

The housing 6 is realized either in a light alloy or a synthetic material capable of withstanding sterilization, since all components of the device must be gas or steam autoclaved. The sliding block 7 is made, for example, of stainless steel.

The sliding surfaces 8 of the housing 6 and/or of the sliding block 7 comprise a slippery covering, not shown in the drawings, for instance nylon or teflon (PTFE).

With reference to FIG. 1 or 2, one will note that the general form of the housing 6 is slightly curved according to the sliding surface 8. The inferior part of housing 6 presents a curved face 9.

A pin 10 fixes the extremity of the rod 2 in the sliding block 7. The extremity of the other rod 3, which is unthreaded, is fitted in a threaded rod 11 and is held in place with two knurled wheels 12 and 13, allowing the adjustment in length of the unit comprising the articulating portion 1 and the rods 2 and 3, whereas any lateral displacement is avoided by means of the extending element 14. The other extremity of the threaded rod 11 cooperates with the housing 6, either by direct screwing, or by means of a pin 15, as illustrated in FIG. 2.

Another component of the articulating portion 1 is a lateral cover 16 whose general shape follows that of the housing 6.

The visible face of that lateral cover 16 presents a scale 17 for the reading of relative angular movements between the sliding block 7 and the housing 6 and its lateral cover 16. Some of the graduations of the rounded scale 17 are enlarged and extended to form viewing lines 18, aiming at the virtual axis A. One could also envisage disposing viewing lines on the side of the housing opposite to the cover 16 (not visible in the drawings).

The scale 17 and its corresponding mentioned numbers on the one hand and the viewing lines 18 on the other can either be painted or engraved in the cover and the housing.

As shown in the detailed cross section of FIG. 7, the side of the housing 6 facing the lateral cover 16 presents an opening 19 corresponding to the sliding block 7. As can be seen in FIG. 2, the opening 19 is rounded to permit the relative movement between housing 6 and sliding block 7. Identically, the cover 16 presents a rounded slot 20, the center of which is also A.

In FIG. 1, the slot 20 is represented with two screws 21 and 22. The first is a locking screw 21, preventing any relative movement between housing 6 and sliding block 7 (see FIG. 7). The second is a limiting screw 22, which is adjusted on the cover along the scale 17, to limit the slot 20 and consequently said relative movement, when the screw 21 is unlocked.

In the first embodiment represented in FIG. 2, the relative movement of housing 6 and sliding block 7 is biased by a spring 23, an extremity of which is fixed in the housing 6 by a pin 24 while the other cooperates with the sliding block 7. In that embodiment, the opening 19 includes an extension 25 in which the spring 23 is localized in the position represented in full lines.

Although not shown in the drawings, any other torsion spring (in shape or disposition) may be used to directly or indirectly cooperate with both housing 6 and sliding block 7.

The means of impeding the movement of block 7 within the housing 6 may alternatively be a rubber strip or ribbon 26, extending through both housing 6 and sliding block 7. In the embodiment presented in FIG. 3, one free end of the rubber strip 26 is held by a metallic ring 27 taking rest on a flat surface 28 provided on the sliding block 7. The other end of the rubber strip 26 is directly fixed to the housing 6 from the outside, by means of a conical screw 29.

Any other fixation of a rubber strip can also be considered without extending beyond the scope of the present invention.

FIG. 4 represents an embodiment using a frictional brake, the force of which can be controlled. This frictional brake is composed principally of:

a fixed part 30, screwed into the housing 6, a stuffing box screw 31, adapted to be screwed on that fixed part 30, and a piston rod 32, sliding in the stuffing box screw 31, an extremity of which extends through the fixed part 30 and cooperates with the sliding block 7, by means of a pin 33 entering in a corresponding opening provided in sliding block 7.

As shown in the detailed FIG. 8, the fixed part 30 and the stuffing box screw 31 both present an extension, 34 and 35 respectively, intended to cooperate with a series of O-rings 36 and pressure rings 37 disposed around the piston rod 32. The section of the pressure rings 37 presents an internal V-shape, the function of which will be explained later on.

The piston rod 32 is made of burnished stainless steel or another well-polished material. The other components of this embodiment are made of materials capable of withstanding sterilization.

The fixed part 30 and the stuffing box screw 31 both present scales, 38 and 39 respectively, for reading the amount of frictional force. The indications of scales 38 and 39 are either painted or engraved.

After the above description of several embodiments of the present invention, the positioning of such a dynamic external bone fixation device will now be explained.

With reference to FIG. 5, the articulating portion is schematized in 1. Using the same reference numbers as in the foregoing description, the rods 2 and 3 are fixed in the ball joints 4 and 5, mounted on two clamps 40 and 41.

The base-plates 42 and 43 of the clamps 40 and 41 are covered by a fiber-reinforced phenolic material to firmly hold the series of pins 44 and 45 disposed in the metacarpus 46 and in the radius 47. One can remark that the base-plates 42 and 43 present holes fitted to exactly position the pins 44 and 45.

With reference to FIG. 6, one can further remark that the fixation device is very near to the fractured member, as the pins 44 are fixed in the second metacarpus 46 with an angulation up to 45°, for clinical reasons which will be detailed later on.

With reference to FIG. 5, the setting up of the device will be detailed.

According to well known techniques, at least two pins 44 are inserted in the second metacarpus 46. The pins 44 can be provided with continuous threads, having a self-drilling point at one end. The opposite end of the pins 44 is designed for secure insertion into a chuck, not represented in the drawings. The self-tapping thread provides maximum gripping power.

Alternatively, one can use non-self-drilling pins, which are inserted in pilot holes through both cortices. Of course, one can employ a guide to obtain the correct disposition of the pins 44.

Both pins 44 in the metacarpus 46 are fixed in the base-plate 42 of the clamp 40.

After approximate alignment of the fracture, at least two pins 45 are similarly inserted in the radius 47 and fixed in the base-plate 43 of the clamp 41.

Both clamps 40 and 41 are provided with ball joints 4 and 5 in which one can fix the extremities of the rods 2 and 3, by means of wing nuts 48 and 49.

When reducing the fracture, the practitioner disposes the device in the correct position by first centering the view lines 18 on the pivot axis of the joint and then fixing the device by means of the wing nuts 48 and 49.

An X-ray may then be taken to determine the correct reduction of the fracture. If necessary, the wing nuts may be loosened and further manipulation may be carried out.

Further adjustment may be realized by means of the knurled wheels 12 and 13, which are first centered on the threaded rod 11 and then displaced to ensure the necessary extension. During initial healing, the device is blocked by means of locking screw 21 (FIGS. 1 and 7).

As already mentioned in the introduction, it is desirable to give progressive motion to the joint after an initial period when the device maintains constant fixation of the fractured member.

Without giving a complete program, one can propose to control the amount of flexion according to the following table:

| | |
|---|---|
| 1st week after fracture | no movement |
| 2nd week after fracture | no movement |
| 3rd week after fracture | flexion up to 10° |
| 4th week after fracture | flexion up to 20° |
| 5th week after fracture | flexion up to 30° |
| 6th week after fracture | flexion up to 40° |

The amount of flexion authorized will be determined by the practitioner who will lock the limiting screw 22 in the corresponding position.

For instance in FIG. 1, the rotation is limited by means of screw 22 to a rotation of 20°, and consequently the relative movement of rods 2 and 3 takes place between the neutral position represented in full lines and the maximum rotation position, represented in dotted lines.

Referring to FIG. 2, one can further note that in the neutral position, represented in full lines, the rods 2 and 3 are not aligned, but form an angle alpha of about 10°. This is due to the normal position at rest of the wrist. The angle of rotation beta represented in this figure is so comprised between 0° and 40°.

As already mentioned, it is significant that the movement during healing can be realized against the influence of a force.

In the embodiment proposed in FIGS. 2 and 3, this force is generally not linear, as neither the spring 23 nor the elastic member 26 creates a reaction of equivalent force according to its position.

To further improve the device, the embodiment of FIG. 4 (detailed FIG. 8) is proposed. In this version the movement is equally biased in both directions as the reactional force is due to the friction of the rod 32 against the O-rings 36.

Furthermore this force can be regulated, either by the patient or by the practitioner, by turning the stuffing box screw 31. Thus when the extensions 34 and 35 come closer together, the O-rings 36 are pressed against the piston rod 32 as they are pressed between the rings 37 whose sectional shape is a V pointing towards the center. Contrarily, the force is reduced when the extensions are separated, as consequently the pressure of the O-rings is reduced.

The graduations of the scales 38 and 39 enable the reading of the value of the friction. The scales 38 and 39 can be so graduated as to form a vernier.

We claim:

1. A dynamic external bone fixation device for the osteosynthesis of a broken joint, comprising:
   (1) a first part comprising a first fixation rod having an axis $a_1$ for connection to bone pins introduced into the bone on one side of said joint,
   (2) a second part comprising a second fixation rod having an axis $a_2$ for connection to bone pins introduced into the bone on the other side of said joint, and
   (3) an articulating portion joining said first part and said second part, said articulating portion comprising:
      (a) a first curved surface to which said first part is connected and which fits with a second curved surface to which said second part is connected so as to allow adjustably limited movement of said first part with respect to said second part, both said first curved surface and said second curved surface having a common virtual axis spaced apart from said device, and
      (b) means for locating said common virtual axis so that said virtual axis may be aligned with the axis of said joint, wherein said means for locating said virtual axis is an integral element of said device.

2. The dynamic fixation device of claim 1 wherein said adjustably limited movement of said first part with respect to said second part is along an arc of a curve and wherein said articulating portion further comprises:
   (a) a housing block fixed to said first fixation rod, said housing presenting said first curved surface and
   (b) a block fixed to said second fixation rod, said block presenting said second curved surface fitting with said first curved surface.

3. The dynamic fixation device of claim 2 wherein said first curved surface and said second curved surface are both portions of substantially cylindrical surfaces having substantially the same virtual axis and having substantially the same radius of curvature, wherein said axis $a_1$ and said axis $a_2$ are substantially coplanar, wherein said device is for the osteosynthesis of a broken wrist, and wherein said device permits motion substantially only in a single plane.

4. The dynamic fixation device of claim 2 further comprising means for limiting the angular sliding movement of said block within said housing.

5. The dynamic fixation device of claim 2 further comprising friction means for loading the sliding movement of said block with a controllable frictional force.

6. The dynamic fixation device of claim 5 wherein said friction means comprises: a piston rod fixed with one end thereof to said block; a bushing screwed into said housing; O-rings placed into said bushing and surrounding said piston rod; pressure rings inserted between two adjacent O-rings; and a stuffing box screw adapted to be screwed by hand into said bushing, thereby compressing said O-rings to a greater or lesser degree and thus controlling said frictional force.

7. The dynamic fixation device of claim 6 wherein said bushing and said stuffing box screw are provided with a vernier.

8. The dynamic fixation device of claim 2 wherein at least one of the curved surfaces of said housing and said block are provided with a slippery layer of material able to withstand repeated sterilizations.

9. A dynamic external bone fixation device for the osteosynthesis of a broken joint, comprising:
   (1) a first part comprising a first fixation rod having an axis $a_1$ for connection to bone pins introduced into the bone on one side of said joint,
   (2) a second part comprising a second fixation rod having an axis $a_2$ for connection to bone pins introduced into the bone on the other side of said joint, and
   (3) an articulating portion joining said first part and said second part, said articulating portion comprising:
      (a) a first curved surface to which said first part is connected and which fits with a second curved surface to which said second part is connected so as to allow adjustably limited movement of said first part with respect to said second part, both said first curved surface and said second curved surface having a common virtual axis spaced apart from said device, and (b) means for locating said common virtual axis so that said virtual axis may be aligned with the axis of said joint, wherein said means for locating said virtual axis is an integral element of said device, and wherein a housing block is fixed to said first fixation rod so that said housing presents said first curved surface, wherein a block is fixed to said second fixation rod such that said block presents said second curved surface which fits with said first curved surface, wherein said first curved surface and said second curved surface are cylindrical surfaces, the axis of the corresponding cylinder being normal to the sliding plane of the sliding block, and wherein said means for locating said virtual axis of said first curved surface comprises viewing lines on said device, and wherein said device comprises also a lateral cover which fits over said housing block and over said block fixed to said second fixation rod and which has a curved slot with a curvature corresponding to the curvature of said first curved surface and the curvature of said second curved surface.

10. The dynamic fixation device of claim 9 wherein said lateral cover is provided with inscriptions indicating the angular displacement of said sliding block.

11. A dynamic external bone fixation device for the osteosynthesis of a broken joint, comprising:
(1) a first part comprising a first fixation rod having an axis $a_1$ for connection to bone pins introduced into the bone on one side of said joint,
(2) a second part comprising a second fixation rod having an axis $a_2$ for connection to bone pins introduced into the bone on the other side of said joint, and
(3) an articulating portion joining said first part and said second part, said articulating portion comprising:
(a) a first curved surface to which said first part is connected and which fits with a second curved surface to which said second part is connected so as to allow adjustably limited movement of said first part with respect to said second part, both said first curved surface and said second curved surface having a common virtual axis spaced apart from said device, and
(b) means for locating said common virtual axis so that said virtual axis may be aligned with the axis of said joint, wherein said means for locating said virtual axis is an integral element of said device, and wherein a housing block is fixed to said first fixation rod so that said housing presents said first curved surface, wherein a block is fixed to said second fixation rod such that said block presents said second curved surface which fits with said first curved surface, wherein said dynamic fixation device further comprises means for biasing said block towards its rest position within said housing in which said first fixation rod and said second fixation rod form a small angle as compared with a straight line of up to about ±10°.

12. The dynamic fixation device of claim 11 wherein said biasing means comprises an elastomer strip fixed with one end to the housing and with the other end to said block.

13. The dynamic fixation device of claim 11 wherein said biasing means comprise a spring inserted between said block and said housing.

14. A dynamic external bone fixation device for the osteosynthesis of a broken joint, comprising: (1) a first part comprising a first fixation rod for connection to bone pins introduced into the bone on one side of said joint, (2) a second part comprising a second fixation rod for connection to bone pins introduced into the bone on the other side of said joint, and (3) an articulating portion joining said first part and said second part, said articulating portion comprising:
(a) curved sliding surface adapted to allow adjustably limited movement of said first part with respect to said second part, said sliding surface having a virtual axis spaced apart from said device, and
(b) means for locating said virtual axis of said curved sliding surface so that said virtual axis may be aligned with said joint, wherein said means for locating said virtual axis is an integral element of said device, and wherein
(1) a housing block is fixed to said first fixation rod, said housing block presenting a convex sliding surface, and
(2) a sliding block is fixed to said second fixation rod, said sliding block presenting a concave sliding surface fitting with said convex sliding surface, and
(3) a lateral cover is present having a curved slot with a curvature corresponding to that of said two sliding surfaces, and wherein said sliding block is fixed to said second fixation rod by means of a pin.

15. A dynamic external bone fixation device for the osteosynthesis of a broken joint, comprising: (1) a first part comprising a first fixation rod for connection to bone pins introduced into the bone on one side of said joint, (2) a second part comprising a second fixation rod for connection to bone pins introduced into the bone on the other side of said joint, and (3) an articulating portion joining said first part and said second part, said articulating portion comprising:
(a) a curved sliding surface adapted to allow adjustably limited movement of said first part with respect to said second part, said sliding surface having a virtual axis spaced apart from said device, and
(b) means for locating said virtual axis of said curved sliding surface, wherein said means for locating said virtual axis is an integral element of said device, and wherein
(1) a housing block is fixed to said first fixation rod, said housing block presenting a convex sliding surface, and
(2) a sliding block is fixed to said second fixation rod, said sliding block presenting a concave sliding surface fitting with said convex sliding surface, wherein said articulating portion has a lateral cover having a curved slot with a curvature corresponding to that of said two sliding surfaces, wherein said dynamic fixation device further comprises friction means for loading the sliding movement of said sliding block with a controllable frictional force, wherein said friction means comprises: a piston rod fixed with one end thereof to said sliding block; a bushing screwed into said housing; O-rings placed into said bushing and surrounding said piston rod; pressure rings inserted between two adjacent O-rings; and a stuffing box screw adapted to be screwed by hand into said bushing, thereby compressing said O-rings to a greater or lesser degree and thus controlling said frictional force.

16. A dynamic fixation device according to claim 15, wherein said bushing and said stuffing box screw are provided with a vernier.

* * * * *